United States Patent [19]

Finley

[11] 4,256,120

[45] Mar. 17, 1981

[54] FLUID SAMPLE COLLECTION DEVICE

[75] Inventor: Michael J. Finley, Richmond Heights, Mo.

[73] Assignee: Sherwood Medical Industries Inc., St. Louis, Mo.

[21] Appl. No.: 109,952

[22] Filed: Jan. 7, 1980

[51] Int. Cl.³ .......................................... A61B 10/00
[52] U.S. Cl. .................................... 128/764; 128/763; 128/766; 233/26; 422/100
[58] Field of Search .............. 128/762, 763, 764, 766, 128/218 NV; 233/26, 1 R; 422/102, 103, 100, 72; 73/425.4 D

[56] References Cited

U.S. PATENT DOCUMENTS

| | | | |
|---|---|---|---|
| 3,159,159 | 12/1964 | Cohen | 128/766 |
| 3,459,177 | 8/1969 | Deuschle | 128/766 |
| 3,706,305 | 12/1972 | Berger et al. | 128/764 |
| 3,771,965 | 11/1973 | Grama | 233/26 |
| 3,838,843 | 10/1974 | Bernhard | 128/218 NV |
| 3,874,367 | 4/1975 | Ayres | 128/218 NV |
| 3,942,514 | 3/1976 | Ogle | 128/764 |
| 3,965,889 | 6/1976 | Sacha | 233/26 |
| 4,112,924 | 9/1978 | Ferrara et al. | 128/764 |
| 4,134,512 | 1/1979 | Nugent | 422/99 |
| 4,207,870 | 6/1980 | Eldridge | 128/764 |

FOREIGN PATENT DOCUMENTS 2349996   2/1974   Fed. Rep. of Germany ........... 128/766

Primary Examiner—William F. Smith
Assistant Examiner—Chris Konkol
Attorney, Agent, or Firm—Stanley N. Garber; William R. O'Meara

[57] ABSTRACT

An evacuated blood sample collection tube is provided with a stopper carrying a one-way valve for preventing blood drawn into the tube from flowing back to the patient, and for preventing blood trapped in the valve after a sample has been taken, from flowing to the sample during centrifugal blood phase separation. The valve includes an elastomeric valve member and a ring member which moves in response to centrifugal forces to a position in which it applies pressure on the valve member to maintain the valve closed during centrifugation.

16 Claims, 8 Drawing Figures

FLUID SAMPLE COLLECTION DEVICE

BACKGROUND OF THE INVENTION

This invention relates to blood sampling devices and more particularly to blood collection devices having anti-backflow valve means.

Evacuated containers or tubes having needle-pierceable stoppers are used extensively in drawing blood samples for clinical testing. A conventional method of obtaining a sample is to employ a blood collection tube, and a tube and needle holder having a double-ended needle cannula. After the distal end of the cannula is placed in the vein of a patient, the tube is moved in the holder until the proximal end of the needle passes through the stopper. The negative pressure in the tube facilitates the drawing of the blood from the vein of the patient. The filled collection tube is subsequently centrifuged to centrifugally separate the blood into its relatively light phase, serum or plasma, and its relatively heavy cellular phase. After phase separation, the light phase is removed for testing. Where serum is to be separated, a blood clot is allowed to form before centrifugation.

When employing conventional collection tubes, faulty techniques in drawing blood can cause drawn blood to be returned to the patient. For example, if the content of the tube is allowed to contact the proximal end of the needle and a tourniquet is not removed soon after blood begins to flow or if the arm of a patient is raised, a drop in venous pressure may cause the backflow of blood from the tube to the patient. Also, if a force is applied to the tube in a manner to compress the stopper against the tube holder while the tube contains blood, a pumping effect may be produced causing withdrawn blood to flow back to the patient. It is, of course, important to prevent the flow of blood drawn back into the patient especially where non-sterile collection tubes are used or where reagents or chemicals are used in the tube for specific test purposes.

Valves have been provided in the needle assembly associated with the tube holder for preventing the backflow of drawn blood to the patient. U.S. Pat. No. 3,874,367, for example, shows a valve disposed in a needle assembly. This construction, however, is relatively expensive since it requires two needles, two hubs, and the steps of securing each needle to its hub.

It is also known to employ a valve in the tube and connected to the tube stopper for preventing the backflow of blood from the tube to the patient. For example, devices having such anti-backflow valves are shown in U.S. Pat. Nos. 4,112,924 and 4,134,512. Such valves generally have a valve chamber into which blood flows from the needle, and a pressure responsive valve member which opens the valve when the pressure in the valve chamber is greater than the pressure in the evacuated tube to thereby allow the blood sample to flow into the tube. Should the fluid pressure in the tube become greater than that in the vein under certain conditions, the valve will prevent backflow of blood from the tube to the patient.

One disadvantage of using such anti-backflow valves of the type shown in the above patents is that some blood remains in the valve chamber after the tube is filled and it is possible or even likely that the valve will open and allow the flow of such blood into the sample sometime during phase separation due to centrifugal forces acting on such blood and the valve. Such blood (or blood clot) could then contaminate the light phase of the blood sample resulting in inaccurate or unreliable blood test results.

In copending application Ser. No. 810,257, filed June 27, 1977, and assigned to the same assignee as this application, a blood collection device is disclosed having a valve constructed such that a blood clot trapped in the valve chamber after the device is filled with a blood sample will tend to be trapped in a narrow passage of the valve so as to reduce the chance of it contaminating serum. However, it is possible under certain conditions that some sample contamination may occur with that device.

SUMMARY OF THE INVENTION

Accordingly, it is an object of the present invention to provide a blood collection device which substantially avoids the above-mentioned undesirable features. A more specific object of the present invention is to provide a blood collection device including a container having a valve therein which prevents blood flow from the container to the source of blood and prevents any trapped blood in the valve from flowing into the blood sample during centrifugation.

In accordance with one form of the present invention, a blood collection device is provided that includes a container having a needle-pierceable stopper closing one end, a collection chamber, and a one-way valve disposed in the container which allows fluid to flow from a blood source and through the needle and valve to the container but prevents fluid flow from the container to the source of fluid, and means responsive to centrifugal forces for maintaining the valve closed during centrifugation of the container.

These, as well as other objects and advantages of the present invention will become apparent from the following detailed description and accompanying drawings.

DESCRIPTION OF THE PREFERRED EMBODIMENT

Figure 1:
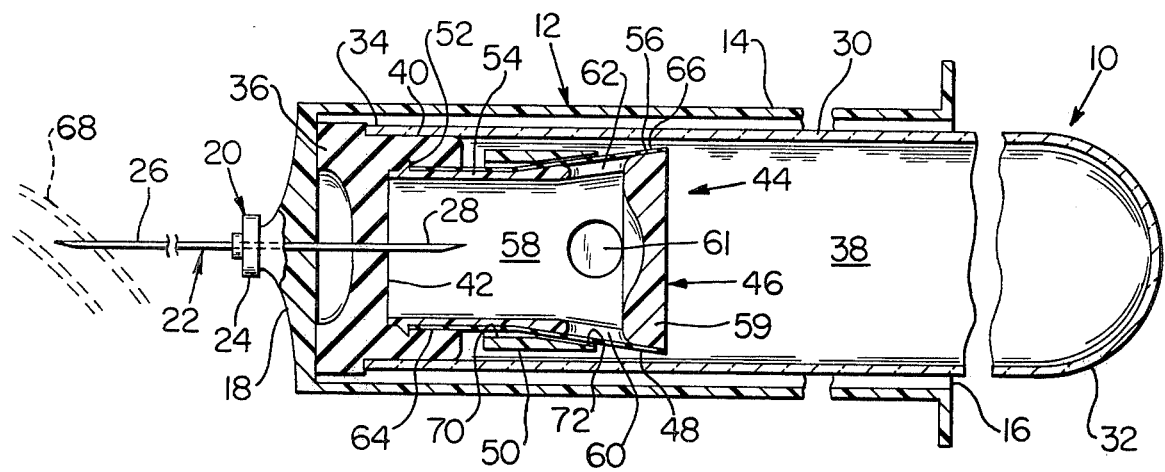
FIG. 1 is a cross-sectional view of a blood collection device in accordance with a preferred embodiment of the present invention with the device being shown disposed in a needle and tube holder.

Referring now to the drawings, and particularly to FIG. 1, a fluid collection device 10 is shown disposed in a conventional tube and needle holder 12. The holder 12 includes a cylindrical portion 14 having an open end 16 for receiving the collection device 10 and a closed end 18 carrying a needle assembly 20 having a double-ended needle cannula or hypodermic needle 22. Needle 22 is fixed to a threaded hub 24 that is threadedly connected to the holder 12. The needle 22, which is pointed at each end, extends longitudinally along the axis of the holder and has a distal end portion 26 exterior to the holder and a proximal portion 28 extending proximally within the cylindrical portion 14.

Collection device 10 is shown including an evacuated blood collection container or tube 30 having an integrally closed bottom or proximal end 32 and an upper or distal open end 34 in which is disposed a needle-pierceable closure stopper 36. Preferably, stopper 36 is formed of a suitable elastomeric or rubber material, such as a butyl compound, conventionally used in blood collection devices, and such that the stopper will maintain a negative pressure within the tube 30 and be self-sealing upon removal of a needle that has pierced the stopper. Tube 30 provides a blood collection chamber 38 within the tube below or proximally of stopper 36. The stopper has a lower cylindrical portion 40 which extends into the tube 26 and which is provided with a bottom central cylindrical recess 42 which is directly below or proximal the central portion of the stopper.

Disposed within the collection tube 30 and extending proximally of the stopper 36 is a one-way, anti-back-flow, fluid pressure responsive valve indicated generally at 44. The valve 44 includes a hollow body member 46 which is received in the stopper recess 42, a resilient valve member 48 on the body member 46, and a valve locking member 50.

The body member 46 has an annular ridge 52 at the distal end which extends radially outwardly and has an outer annular sharp edge which frictionally engages the inner cylindrical wall of the recess 42 of the stopper to fix the valve 44 in place in the bottom of the stopper. The distal end of the valve body 46 is shown engaging the bottom of the stopper recess 42.

Figure 2:
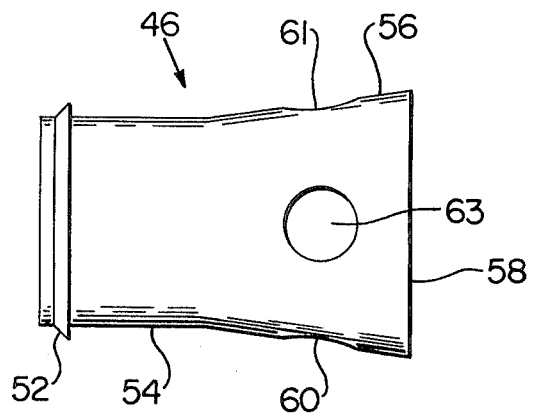
FIG. 2 is an enlarged side view of the valve body in FIG. 1.

The hollow body member 46, as also seen in FIG. 2, has a distal cylindrical portion 54 integrally connected to a generally conical or radially outwardly flaring proximal portion 56 having its maximum diameter at the proximal end. The portions 54 and 56 form a valve chamber indicated at 58. Portion 56 is shown having a closed bottom or proximal end wall 59 and four openings 60, 61, 62 and 63 circumferentially spaced 90° apart and extending through the sidewall of the body portion 56 and connected with valve chamber 58.

Figure 3:
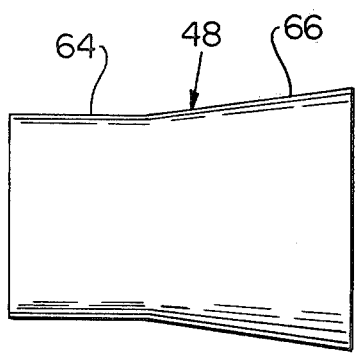
FIG. 3 is an enlarged side view of the resilient valve member of FIG. 1.

The resilient valve member 48 is shown as an elastomeric or rubber-like sleeve normally covering and closing body sidewall openings 60–63. Valve member 48 is formed to have an unstressed shape substantially complementary to the outer sidewall surface of the valve body 46 as seen in FIG. 3. Sleeve 48 may be made of any suitable elastomeric material, for example, polyurethane. The valve sleeve 48 has a cylindrical portion 64 and a conical portion 66 which closely surrounds the body member portions 54 and 56, respectively, as seen in FIG. 1. When on the valve body 46, the sleeve 48 provides a close fit which closes the four sidewall openings 60–63 in the valve body 46, but with only slight pressures applied to the body at the sidewall openings. That is, the sleeve is only slightly stretched over the conical body portion 56 so that while the sidewall openings are closed in the absence of any pressure differential across the sleeve at the openings, even a slight pressure on the interior side of the sleeve, that is, on the valve chamber 58 side of the sleeve 48, relative to that on the outer or exterior side of the sleeve, or that within the collection chamber 38, will cause the sleeve to move away from one or more of the sidewall openings 60–63 and open the valve 44. On the other hand, any pressure differentials which are of reverse nature, that is, where a greater pressure exists on the exterior side of the sleeve 48 than on the interior side of the sleeve, increase the pressure tending to close the valve openings 60–63.

The valve locking member 50 is shown in the form of a ring having its minimum inner diameter slightly greater than the outer diameter of the cylindrical valve sleeve portion 64 when the sleeve 48 is initially disposed on the valve body 46 as seen in FIG. 1. With this relationship, the ring is loosely disposed in surrounding relation with the body member 46 and sleeve 48. Ring 50 has a distal cylindrical inner wall 70 connecting with a proximal generally conical wall portion 72 having its maximum inner diameter at the proximal end. The wall portion 72 is shown having an incline similar to that of the outer surface of the sleeve portion 66.

In FIG. 1, the valve locking ring 50 is loosely disposed on the valve and does not interfere with the operation of the valve, that is, it does not prevent the valve from opening when a blood sample is taken or prevent the valve from functioning to prevent the backflow of blood from the tube 30 to the patient should the pressure in collection chamber 38 exceed that in the vein of the patient.

Figure 4:
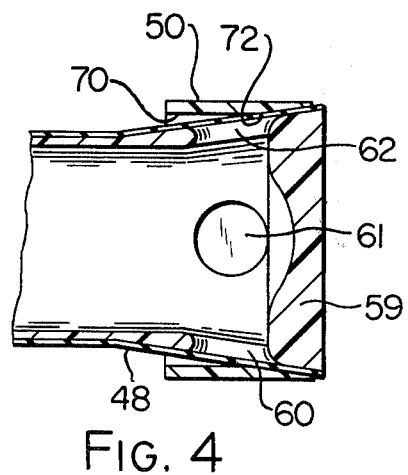
FIG. 4 is an enlarged fragmentary cross-sectional view of the device of FIG. 1 but with the locking member moved to its valve locking position.

The valve locking ring 50 is movable from its loose or inactive condition or position on the valve sleeve 48 (FIG. 1), to a valve locking position shown in FIG. 4. In FIG. 4, the valve 44 is secured in its closed position by the ring such that no blood can flow in either direction through any of the sidewall openings 60–63 or between the valve and collection chambers 38 and 58. The ring 50 is movable between its inactive and locking positions in response to centrifugal forces generated during centrifugation of the blood filled collection tube 30, as will be discussed hereafter. In the valve locking position, the inclined inner wall 72 of ring 50 clamps the proximal end portion of the valve sleeve portion 66 against the outer peripheral surface of the proximal end portion of the valve body or end wall 59 to seal the valve chamber 58 from the collection chamber 38. The sleeve portion 64 extends distally a distance sufficient to prevent blood from flowing between body portion 54 and sleeve portion 64 under any operating conditions.

The ring 50 may be made of a metal, such as brass, or other material such as a suitable plastic material. For example, the ring 50 may be molded of a suitable relatively hard plastic such as an acrylic containing a filler, such as silica, or other material which will cause the ring to have an adequate density. The density of the ring 50 should be great enough to cause the ring to move from its initial loose condition (FIG. 1) to its valve closing or locking position (FIG. 4) and provide a sufficient pressure on the sleeve 48 to maintain the valve closed during centrifugation of the filled tube.

In use, the pointed end of the distal portion 26 of needle 22 is inserted into a source of fluid, such as in the vein of a patient, indicated in phantom at 68 in FIG. 1, and the blood collection tube 30 is moved distally along the cylinder 14 until the stopper engages the distal end wall 18 of the holder. During this movement, the inner portion 28 of needle 22 pierces stopper 36 and enters the valve chamber 58. Because of the difference in fluid pressures in the vein and collection chamber 38, blood flows from the vein 68 into valve chamber 58, through one or more openings 60–63 in valve body member 46, and into chamber 38. Because of the pressure differentials across the valve sleeve 48, the sleeve moves radially outwardly away from the body member at one or more of the openings allowing blood to flow between the proximal end portions of the sleeve 48 and the valve body 46. Since valve locking member 50 is in its inactive position spaced generally distally of the sidewall openings 60–63 during the taking of a blood sample, it does not, in any way, interfere with the flow of blood from the vein and needle 22 into the valve chamber 58, through the valve sidewall openings and into the collection chamber 38. Any tendency for blood to flow during the sample taking step from the collection chamber 38 back into the valve chamber 58 and into the needle to the patient, is prevented by the closing of the elastic sleeve member 48 against the body member 46 about the openings 60–63.

When the tube 30 has been filled with the blood sample, the tube 30 is removed from holder 12 and generally allowed to stand, for example, for a half-hour to an hour, to permit a blood clot to form where serum is to be separated from the whole blood. After a blood clot has formed, the collection tube 30 is placed in a centrifuge and centrifuged for a time sufficient to separate the relatively light phase or serum from the heavier cellular phase. When desired, known automatic phase separating devices or gel-like sealant materials may be employed to automatically provide a barrier at the interface of the separated serum and cellular phases after separation.

When the blood filled tube 30 is placed in the centrifuge and the centrifuge is turned on, the locking ring 50 is moved by centrifugal forces to its valve locking position (FIG. 4). Because of the complementary conical surfaces 56, 66 and 72 of the body member 46, sleeve 48, and ring 50, respectively, the ring seats firmly over the sleeve maintaining the valve closed during the continued centrifugation of the tube. Thus, no blood that is trapped in the valve chamber 58 can escape to the sample in chamber 38 during centrifugation. After complete phase separation, the tube may be removed from the centrifuge and the light phase removed from the tube for clinical testing purposes.

In the modified embodiment shown in FIGS. 5–8, an anti-backflow valve 80 is shown frictionally secured in a recess 82 of a stopper 84 of an evacuated collection tube 86 by a sharp annular ridge 87 on the valve. The valve 80 includes a valve body 88 including a main generally cylindrical body member 90 and an end cap or base member 92 connected by a central screw 94 to the proximal end of the body 90. Valve 80 also includes annular resilient valve member or seal 96, and a slidable, centrifugally actuated valve locking member or ring 98.

Figures 6, 7:
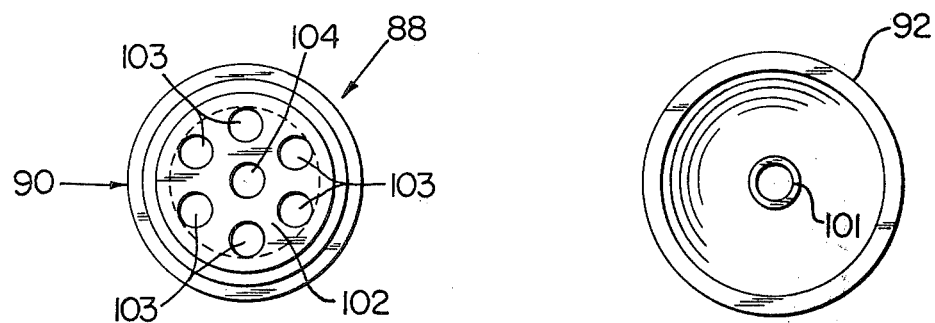
FIG. 6 is a right end view of a port of the valve body member of FIG. 5.
FIG. 7 is a left end view of another part of the valve body of FIG. 6.

The valve body 90 is hollow and provides a valve chamber 100, and has an end wall 102 at the proximal end which has a plurality of circumferentially spaced axial openings 103 and a central threaded hole 104 for receiving screw 94, as best seen in FIG. 6. The valve body 90 is open at both ends and has a proximal end portion 105 with a reduced outer diameter. The cap 92, seen also in FIG. 7, is generally cup-shaped and is connected by means of screw 94 passing through a threaded central opening 101 in the cap in telescoping relation with the valve body 90. The inner diameter of the cap 92 at its distal end is greater than the outer diameter of the proximal end portion 105 of the valve body 90 providing an annular blood flow passage 106 between the body and cap members 90 and 92. The resilient valve member 96 is shown in the form of an annular sealing ring sealingly engaging and surrounding the proximal end portion 105 of valve body 90 and engaging the distal end of cap 92 to normally close passage 106 against the flow of fluid between the valve chamber 100 and the blood collection tube chamber indicated at 108. The proximal end of the sealing ring 96 is notched to provide an annular end wall L-shaped in cross-section which receives the distal end wall of the cup-shaped cap 92. The inner diameter of the sealing ring at the distal end is substantially less than its inner diameter at it proximal end, the distal end providing a sealing lip 109. The sealing ring 96 also has an outer conical or tapered surface 110 that tapers from its distal end radially outwardly to its proximal end.

Figure 8:
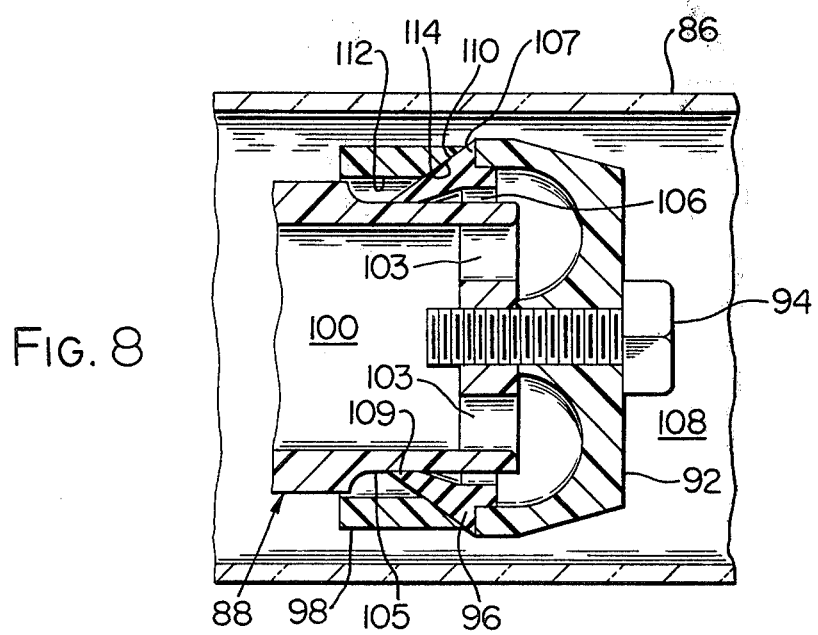
FIG. 8 is an enlarged fragmentary cross-sectional view of the device of FIG. 5 but with the valve locking member in a valve closing position.

The valve locking ring 98, seen also in FIG. 8, has an inner cylindrical wall surface 112 connected to a proximal conical or tapered wall surface 114 which is complementary in shape to outer tapered wall surface 110 of the sealing ring 96. The ring 96 may be made, for example, of a suitable elastomeric material such as a suitable butyl rubber or other rubber-like material. The locking ring 98 may be made of the same material as that of the locking ring 50 of FIG. 1.

Figure 5:
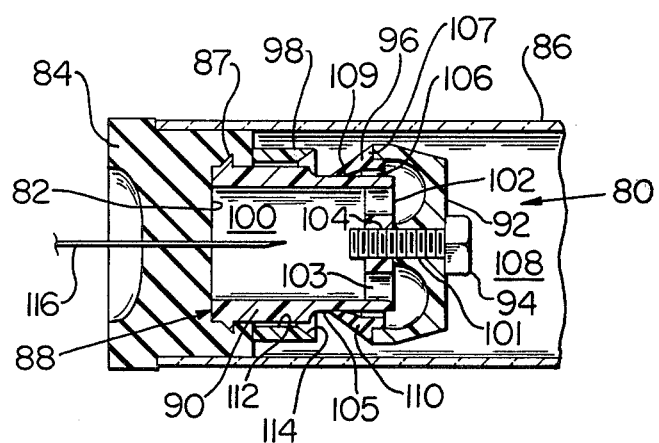
FIG. 5 is a fragmentary cross-sectional view of a modified blood collection device in accordance with another preferred embodiment of the present invention.

When a blood sampling needle, indicated at 116 in FIG. 5, is inserted through stopper 84 and into valve chamber 100, the fluid pressure differential across the valve or between chambers 100 and 108 causes the L-shaped portion 107 of the sealing ring 96 to move away from the annular distal end of cap 92 and allow blood to flow in passage 106. Blood flow from the needle and valve chamber 100 to the blood collection chamber 108. The sealing ring portion 107 will close the valve or passage 106 in the event of a pressure reversal that would tend to allow blood to flow back to the patient.

After the collection tube 86 is filled, it is subsequently placed in a centrifuge to centrifugally separate the blood phases. After the centrifuge is started, the centrifugal forces acting on the locking ring 98 move it proximally into the position shown in FIG. 8 wherein the locking ring applies a clamping force on the inclined surface 110 of the sealing ring 96. The ring 98 then holds the sealing portion 107 against the valve body and cap to prevent any blood or blood clot remaining in the valve body chamber 100 or cap 92 from moving through the passage 106 past portion 107 to the collection chamber 108. Thus, during centrifugation, any blood that was trapped in the valve during the filling of the collection tube cannot enter the blood sample portion of the tube regardless of the centrifugal forces encountered during centrifugation.

It will be apparent that in both embodiments described herein, that any blood or blood clot formed and trapped in the valve is positively prevented from moving into the blood collection portion of the tube during centrifugation by the described centrifugally actuated valve securing or locking means. Thus, such trapped blood cannot contaminate the sample. After phase separation, the separated light phase, serum or plasma, will be prevented by the elastomeric sealing sleeve or ring from contacting the blood trapped in the valve. Also, if the tube is opened to remove the serum after centrifugation, any blood trapped in the valve is maintained within the sealed valve chamber and is removed when the stopper is removed from the tube.

The relatively movable valve members, that is, the valve body and elastomeric sealing ring, of each embodiment, are constructed, as described, so that each is a one-way valve allowing fluid flow only from the needle to the collection chamber so as to avoid blood reflux or blackflow from the device to the patient. Preferably, the valves are normally closed as shown. The resilience of the elastomeric sealing members 48 and 96 provide the slight biasing force maintaining the valves normally closed. Also, in both of the illustrated embodiments, the elastomeric sealing ring has a pressure applied by the valve securing or locking member, or is clamped thereby, in a valve closing direction against the valve body upon centrifugation of the blood containing tube. In this way, during continued centrifugation, no blood can flow from the valve to the collection chamber since the valve is ensured against opening by the securing member. The locking members or rings 50 and 98 have an inner diameter relative to the outer diameter of the valve body, or are sized, such that the ring can move from its normally loose inactive position (FIGS. 1, 5) about the valve body to its valve closing or locking position (FIGS. 4, 8). The complementary inclined surfaces of the elastomeric valve member and the securing ring provide good transfer of pressure to the sealing areas of the valve member during centrifugation of the device.

As various changes could be made in the above construction without departing from the scope of the invention, it is intended that all matter contained in the above description or shown in the accompanying drawings shall be interpreted as illustrative and not in a limiting sense.

What is claimed is:

1. A blood sample collection device adapted to receive a blood sample and to be centrifuged for separating the blood phases comprising an evacuated container, a stopper closing one end of said container, and a valve in said container between said stopper and the opposite end of said container defining a first chamber between said stopper and said valve, and a second chamber between said valve and said opposite end of said container, said stopper being pierceable by a needle for connecting a source of blood in fluid communication with said first chamber, said valve being responsive to fluid communication with said source of blood to open said valve and allow blood to flow therethrough to said second chamber, and valve securing means in said container responsive to centrifugal forces upon centrifugation of said container to maintain said valve closed during continued centrifugation of said container.

2. The device of claim 1 wherein said valve is a one-way valve which allows the flow of fluid therethrough in response to a fluid pressure in said first chamber which is greater than the fluid pressure in said second chamber, and which is closed in response to a fluid pressure in said second chamber that is greater than that in said first chamber.

3. The device of claim 2 wherein said valve is secured to said stopper within said container.

4. The device of claims 1, 2 or 3 wherein said valve includes a pair of relatively movable valve members normally in resilient biased engagement closing said valve, said valve members being relatively movable in response to said fluid communication with the source of blood to open said valve, and wherein said valve securing member applies a pressure on said members in a direction closing said valve upon centrifugation.

5. The device of claim 3 wherein said valve includes a pair of relatively movable valve members, one of said valve members has a fluid flow passage therethrough connecting said first and second chambers, and said other valve member is normally in a position sealingly closing said passage to close said valve, and said valve securing means is movable into engagement with said other valve member to prevent movement thereof from said position during centrifugation of said container.

6. The device of claim 5 wherein said second valve member is a generally annular member of elastomeric material.

7. A blood sample collection device adapter to receive a blood sample and to be centrifuged for separating the blood phases comprising an evacuated container having a collection chamber therein, a needle-pierceable stopper closing one end of said container, and a one-way valve in said container between said stopper and said collection chamber, said valve including a valve body having a valve chamber adapted to be connected in fluid communication with a needle when the needle is used to pierce said stopper and transfer blood to said container from a blood source, said valve having fluid passage means therein for the flow of fluid from said valve chamber to said collection chamber, valve means normally closing said passage means and responsive to a fluid pressure in said valve chamber to open said passage means and allow fluid flow from said valve chamber to said collection chamber, and valve securing means responsive to centrifugal forces upon centrifugation of said container for preventing said valve means from opening said passage means to the flow of blood to said collection chamber during centrifugation.

8. The device of claim 7 wherein said valve means comprises an elastomeric member normally resiliently closing said passage means against fluid flow therethrough, and said securing means comprises a member engageable with said elastomeric member and applying a pressure thereto in response to said centrifugal forces to urge said member in a valve closing direction.

9. The device of claims 7 or 8 wherein said valve body is secured to said stopper.

10. The device of claim 9 wherein said valve body includes a conical portion, said passage means is provided in a sidewall of said conical portion, said valve means includes an elastomeric sleeve surrounding said conical portion and said passage means to normally close said passage means, and said valve securing means includes a member having a conical inner surface movable over said conical portion to apply a force to said sleeve adjacent said passage means to maintain said passage means closed in response to said centrifugal forces.

11. The device of claim 10 wherein said valve securing means comprises a ring clamping portion of said sleeve against said conical portion of said valve body in response to said centrifugal forces.

12. The device of claim 7 wherein said valve securing means includes a ring surrounding said valve body and sized for axial movement thereon from a normal inactive position to a valve locking position in response to said centrifugal forces.

13. The device of claims 7 or 12 wherein said stopper has a recess facing said end of said container opposite said one end, said valve body being received in said recess and having means on the outer surface thereof frictionally engaging the sidewalls of said stopper recess for securing said valve thereto.

14. The device of claim 9 wherein said passage means includes a passage extending distally toward said stopper, said valve means includes an annular resilient elastomeric ring normally engaging and surrounding said valve body adjacent the distal end of said passage, said elastomeric ring having a portion movable from said valve body to allow fluid flow through said passage in response to a predetermined fluid pressure in said valve chamber, and said valve securing means includes an annular member movable in response to said centrifugal forces into tight clamping engagement with said elastomeric ring to lock said ring in a passage closing condition to prevent said valve means from allowing fluid flow through said passage during centrifugal phase separation of the blood sample.

15. The device of claim 14 wherein said elastomeric ring has a radially outer conical surface, and said valve securing means has a conical inner surface complementary to and engageable with said conical surface of said elastomeric ring when locking said valve means in the closed condition.

16. The device of claim 14 wherein said body member includes a cylindrical portion and a cup-shaped portion in telescoping relation with said cylindrical portion, said passage being defined between radially spaced parts of said portions.

* * * * *